US008683849B2

(12) United States Patent  
Giardino et al.

(10) Patent No.: US 8,683,849 B2
(45) Date of Patent: Apr. 1, 2014

(54) METHOD AND APPARATUS FOR TESTING CONSISTENCY OF FROZEN BEVERAGES

(75) Inventors: Nicholas M. Giardino, Gilberts, IL (US); Derek Choi, New Haven, CT (US); Lawrence Oetjens, Bloomingdale, IL (US); Andrew J. Tobler, Franklin Park, IL (US); E. Scott Sevcik, Crystal Lake, IL (US)

(73) Assignee: IMI Cornelius, Inc., Glendale Heights, IL (US)

( * ) Notice: Subject to any disclaimer, the term of this patent is extended or adjusted under 35 U.S.C. 154(b) by 318 days.

(21) Appl. No.: 12/930,563

(22) Filed: Jan. 11, 2011

(65) Prior Publication Data

US 2011/0226046 A1 Sep. 22, 2011

Related U.S. Application Data

(60) Provisional application No. 61/335,787, filed on Jan. 12, 2010.

(51) Int. Cl.
*G01N 3/42* (2006.01)

(52) U.S. Cl.
USPC ............. 73/81; 73/12.09; 73/12.13; 73/78; 73/85

(58) Field of Classification Search
USPC ........... 73/12.09–12.13, 54.01–61.79, 78–82, 73/85
See application file for complete search history.

(56) References Cited

U.S. PATENT DOCUMENTS

| 1,586,363 | A | * | 5/1926 | Hall | 73/79 |
|---|---|---|---|---|---|
| 1,762,639 | A | * | 6/1930 | Pierre | 73/79 |
| 2,716,884 | A | * | 9/1955 | Rosenberg | 73/12.01 |
| 2,892,342 | A | * | 6/1959 | Goss et al. | 73/12.13 |
| 3,266,289 | A | * | 8/1966 | Stamy | 73/12.13 |
| 3,426,578 | A | * | 2/1969 | Bergs et al. | 73/12.06 |
| 3,535,122 | A | * | 10/1970 | Mussellwhite et al. | 426/565 |
| 3,859,841 | A | * | 1/1975 | Evans et al. | 73/11.04 |
| 4,199,604 | A | * | 4/1980 | Kahn et al. | 426/327 |
| 4,400,406 | A | * | 8/1983 | Morley et al. | 426/565 |
| 4,452,823 | A | * | 6/1984 | Connolly et al. | 426/115 |
| 4,531,400 | A | * | 7/1985 | Nevel | 73/12.13 |
| 4,542,639 | A | * | 9/1985 | Cawley et al. | 73/12.09 |
| 4,640,120 | A | * | 2/1987 | Garritano et al. | 73/12.13 |
| 4,880,657 | A | * | 11/1989 | Guffey et al. | 426/601 |
| 4,987,766 | A | * | 1/1991 | Brar et al. | 73/12.13 |
| 4,988,529 | A | * | 1/1991 | Nakaya et al. | 426/569 |
| 5,037,660 | A | * | 8/1991 | Driessen et al. | 426/43 |
| 5,095,710 | A | * | 3/1992 | Black et al. | 62/68 |
| 5,306,516 | A | * | 4/1994 | Letton et al. | 426/531 |
| 5,390,535 | A | * | 2/1995 | Smock et al. | 73/79 |
| 5,454,264 | A | * | 10/1995 | Lampinen et al. | 73/12.06 |
| 5,739,411 | A | * | 4/1998 | Lee et al. | 73/12.13 |
| 5,869,125 | A | * | 2/1999 | Lynch et al. | 426/603 |

(Continued)

FOREIGN PATENT DOCUMENTS

DE 3138427 A1 * 5/1983 ............... G01N 3/14
WO WO 2009133067 A1 * 11/2009

*Primary Examiner* — David A Rogers
(74) *Attorney, Agent, or Firm* — Niro, Haller & Niro

(57) ABSTRACT

A method and apparatus using a sample test container filled with beverage, a penetrator holder, a penetrator and release means is disclosed. In the method a sample, is drawn into the test container and the penetrator dropped into the sample, and a reading of the stiffness of the sample is made based on the depth of penetration of the penetrator onto the sample.

18 Claims, 15 Drawing Sheets

(56) References Cited

U.S. PATENT DOCUMENTS

| | | | |
|---|---|---|---|
| 6,163,095 A | 12/2000 | Shams et al. | |
| 6,220,047 B1 | 4/2001 | Vogel et al. | |
| 6,365,175 B1 * | 4/2002 | Alaluf et al. | 424/439 |
| 7,284,414 B2 * | 10/2007 | Wu | 73/79 |
| 7,351,438 B2 * | 4/2008 | Sozzi et al. | 426/3 |
| 7,430,892 B2 * | 10/2008 | McNamara et al. | 73/12.13 |
| 7,617,718 B2 * | 11/2009 | Kinast et al. | 73/84 |
| 7,900,499 B2 * | 3/2011 | Zhang | 73/12.13 |
| 2001/0010170 A1 * | 8/2001 | Sato et al. | 73/79 |
| 2006/0130566 A1 * | 6/2006 | Wu | 73/82 |
| 2008/0038438 A1 * | 2/2008 | Moore et al. | 426/576 |
| 2010/0064783 A1 * | 3/2010 | Stein | 73/81 |

\* cited by examiner

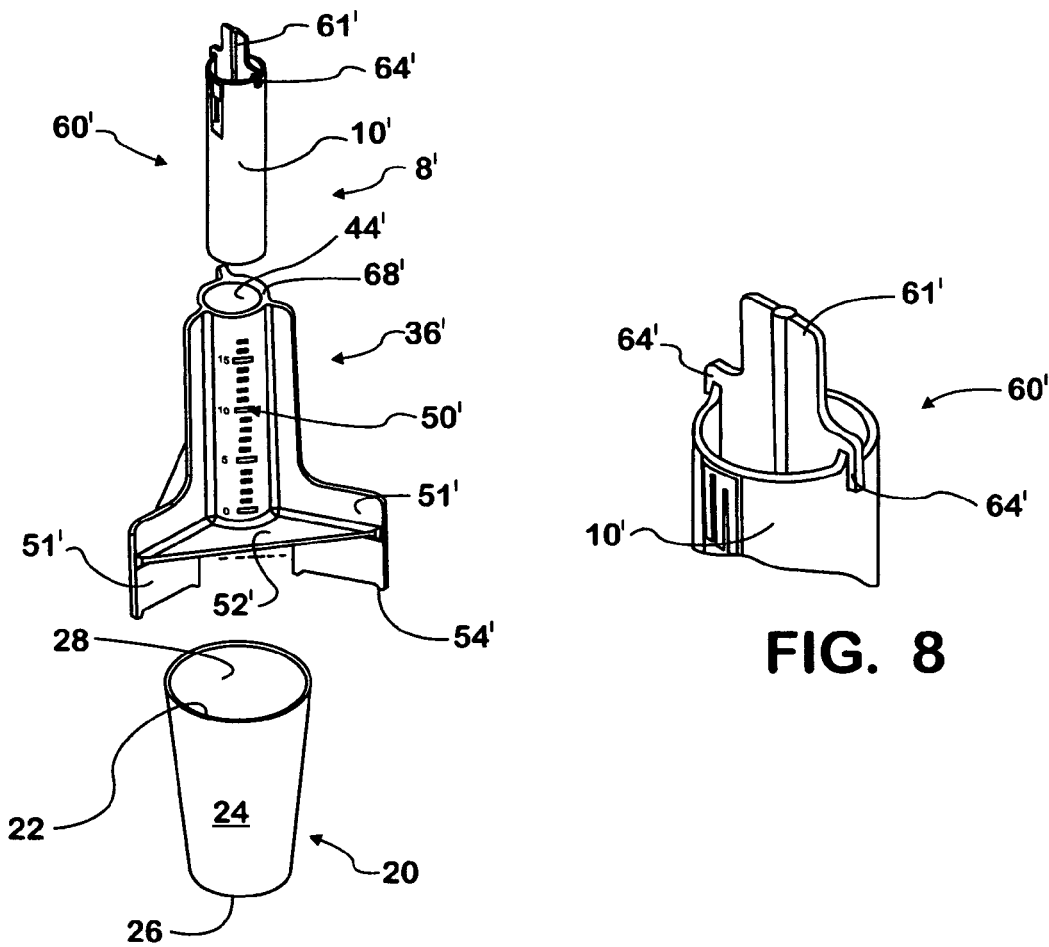
FIG. 7
FIG. 8
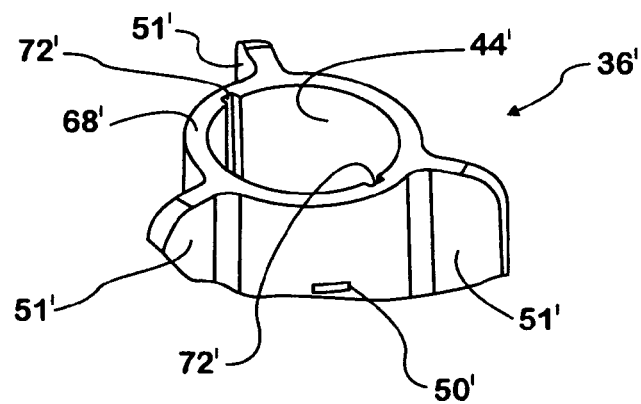
FIG. 9

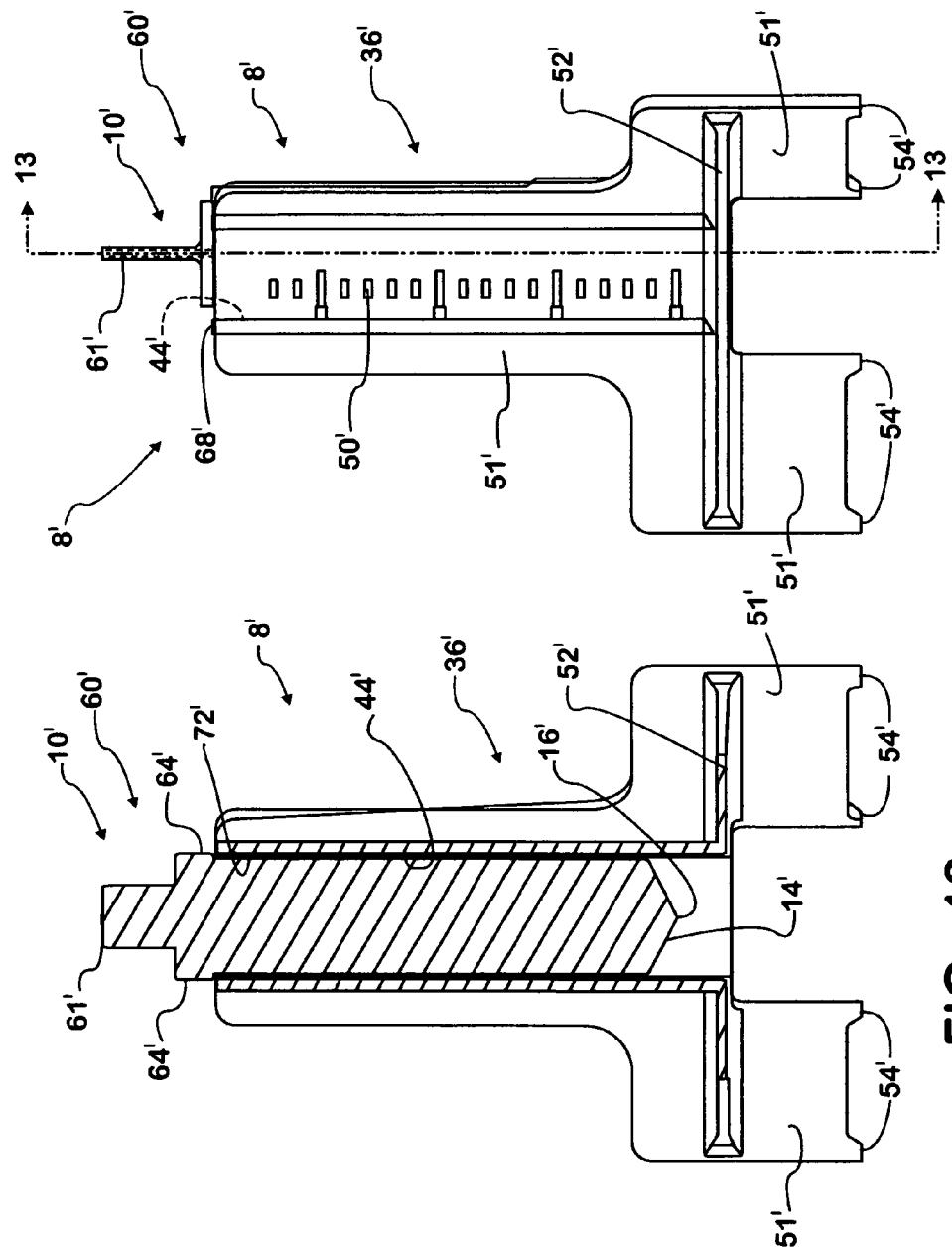

PENETROMETER DAIRY

PENETROMETER NON-DAIRY

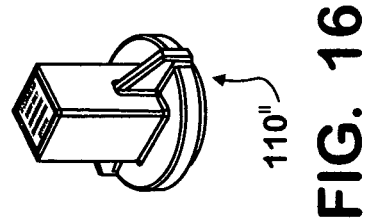
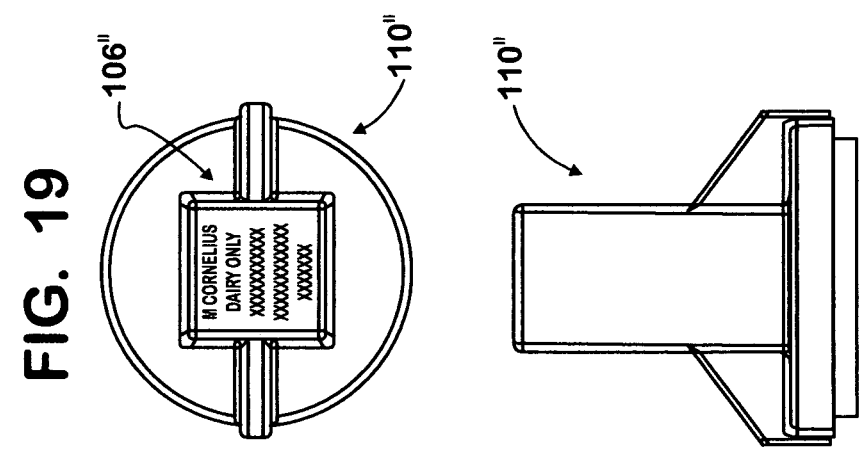
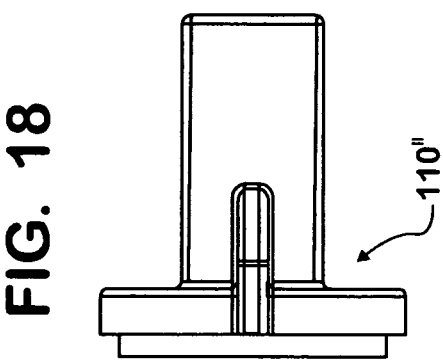

METHOD AND APPARATUS FOR TESTING CONSISTENCY OF FROZEN BEVERAGES

This application is a United States Nonprovisional Patent Application claiming the priority, filing date and benefit of U.S. Provisional Patent Application Ser. No. 61/335,787, filed on Jan. 12, 2010, of the same title, which is herein incorporated by reference, and relates to methods and apparatus for testing the consistency of frozen (also known as semi-frozen) beverage, such as carbonated and uncarbonated semi-frozen beverages.

BACKGROUND OF THE INVENTION

Heretofore semi-frozen beverages have been dispensed and attempts have been made to control the consistency of the same by controlling the ingredients (flavor syrups, water/ice and carbonating $CO_2$ gas (carbonated beverage-forming a FCB) or air (noncarbonated-forming a non FCB). An example of a machine for making such a beverage is shown in U.S. Pat. Nos. 6,163,095 and 6,220,047.

Not only are the ingredients controlled; but the ratio of such ingredients to each other are controlled. Other approaches include trying to control the temperature of the mixture prior to the dispense. Even with close control of the ingredients, their relative ratios and temperature, such may not accurately predict the consistency or stiffness of the dispensed mixture which can still vary.

SUMMARY OF THE INVENTION

The present invention relates to the method and apparatus for testing and establishing the consistency and stiffness of the dispensed mixture to provide guidance as to establishing a consistent semi-frozen beverage. This apparatus and method allow for a frozen beverage to be measured respective to its frozen consistency. The apparatus or device of the present invention provides a simple and accurate low cost tool and operating procedure that can be used in the field or beverage lab to determine the drink's consistency attribute. The consistency attribute can otherwise be defined, called or known as viscosity, consistency, flowability, stiffness or thickness. It is important to measure a frozen beverage consistency because a frozen drink can have similar weight and temperature but be physically different in regards to its frozen percentage, consistency, or ice fraction. A test procedure that measures the frozen consistency will help improve the quality of drinks served to consumers.

The device includes a dropping mass or penetrator that when triggered is dropped or generally free falls from a fixed and known height or distance and penetrates into the frozen beverage. The test procedure uses and is also specific to measuring in the cup that typical drinks are poured into, of low cost, and transparent. The dropping mass is associated with indicia or graduations that can be visibly read. The graduations can also be color coded to provide a graded (good to bad) reference indication. When measuring drinks of similar consistency, the graduations exposed or buried into the frozen slush should be repeatable if the drinks are of the same consistency. If the drink is wetter or less frozen or stiff, then the penetrating mass will submerge deeper into the frozen beverage in the cup and the indications will be different but relative to that drink quality. To aid accuracy of testing the penetrator is dropped from a penetrator holder or launch tube a fixed distance. The graduations may be provided on the launch tube or penetrator. In the test the penetrator is placed on the launch tube and the latter located on the standard size, disposal cup the frozen beverage, say an FCB, is usually dispensed in.

The operating procedure is to drop the mass and count the graduations exposed from the top of the launching tube. The typical penetrator could be of a mass of 70 g or 100 g and made of say ABS or polycarbonate plastic. The dropping penetrating mass could be of different weights and sanitary easily cleaned materials. The penetrator could have different shapes for different beverages or slushies, say sharp ended for front slushies and blunt ended for pure liquid juice or dairy slushies. The end angles could vary from 40° to 140° and say +/−10, for the non-dairy and dairy beverages, respectively.

A trigger means can be provided for launching the penetrator. In one version the trigger means could be in the form of a cross member or pin. The cross member is used to hold the penetrator or dropping mass at the top of the launch tube. The cross member could also be inserted into the launch tube at different elevations to control the drop height distance. Upon removal of the cross member or pin, it releases the penetrator to fall into the beverage. Another form of trigger means for launching could be cooperating tabs and slots to permit the penetrator to fall through the launch tubes where the tabs and slots are moved from a non-aligned support position of the penetrator on the launch tube to an aligned (falling or dropping) position.

The method comprises establishing a standard procedure for drawing off and striking a sample of semi-frozen beverage, forming a standard sample in a standard container, usually the disposable transparent cup used to dispense the frozen beverage or FCB, measuring the temperature of the standard sample, and then subjecting the standard sample to a penetration test of dropping a known penetrator (in weight and shape) from a fixed or known height from the penetration holder or launch tube into the standard sample, causing the penetrator to penetrate the beverage and measuring, preferably directly off a scale on one of the penetration holder, the penetrator, or sample container, the depth of penetration onto the standard beverage sample. If need be, a guidance table (see FIG. 6) can be consulted which will relate the depth of penetration to non FCB or FCB machine adjustments to achieve a desired consistency.

As noted, the apparatus comprises a standard sample container, a penetrator, a launch tube or stand for holding the penetrator a known and fixed distance above the surface of the sample, and a trigger or release means to drop in a consistent manner the penetrator into the sample. The penetrator could be of different lengths for different beverages, say longer for the non-dairy slushies to account for the sharp end and shorter for dairy slushies to account for the blunt end. Then construction would also give a different drop height to the sample top surface, shorter for the dairy and longer for the non-dairy.

BRIEF DESCRIPTION OF THE DRAWINGS

FIG. 7 is a perspective view of a second preferred embodiment, including a penetrator, launch tube and standard cup.

FIG. 8 is an enlarged perspective view of the detail of the top portion of the penetrator of FIG. 7 showing its support tabs forming part of the trigger means.

FIG. 9 is an enlarged perspective view of the cooperating detail forming part of the trigger means on, the top portion of the launch tube of FIG. 7, and its cooperating slots, upon which the penetrator and particularly the support tabs portion shown in FIG. 8 is supported.

FIG. 12 is an elevational view of the second embodiment showing the penetrator inside and supported on the launch tube and shows the measurement indicia, in this instance, on the launch tube.

FIG. 13 is a cross sectional view taken on the line 13-13 of FIG. 12.

FIG. 16 shows a perspective view of the top piece for FIG. 15 before assembly, a similar top but of a different color and indicia is used with the "non-dairy" embodiment shown in FIGS. 24-27.

FIG. 17 is an elevational front view of the top piece shown in FIG. 16.

FIG. 18 is an elevational side view of the top apiece shown in FIG. 16.

FIG. 19 is a top view of the top piece shown in FIG. 16.

DESCRIPTION OF PREFERRED EMBODIMENTS

Figure 1:
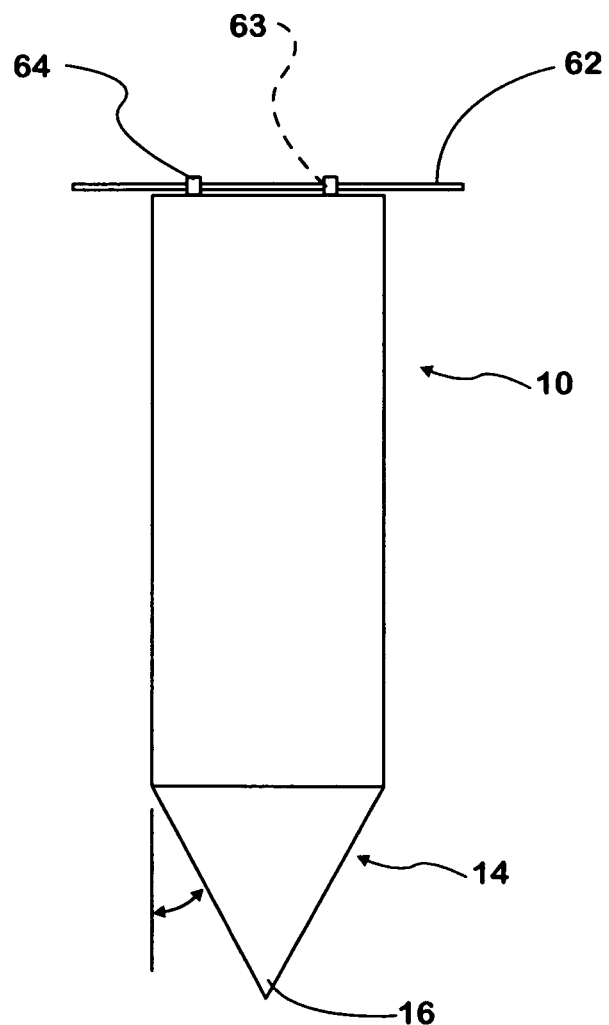
FIG. 1 shows a first embodiment penetrator for the present invention.

Referring to FIG. 1, the apparatus 8 (see FIG. 3) of the present invention includes a penetrator or drop weight 10, which is of a fixed cross-section, such as round or square) of a fixed length (say 6 inches) and of a fixed known weight (say 70 or 100 grams) and a fixed standardized penetrator end 14, having a downward pointed end 16 of about 40 degrees plus or minus 5 degrees to or about 140 degrees plus or minus 5 degrees. The specific preferred angle is dependent on the type of product being tested. An angle of about 40 degrees plus or minus 10 degrees is preferred for a dairy product and an angle of about 140 degrees plus or minus 10 degrees is preferred when testing a fruit slushy type beverage. This angle is the included angle from one surface of the tip to the other.

Figure 2:
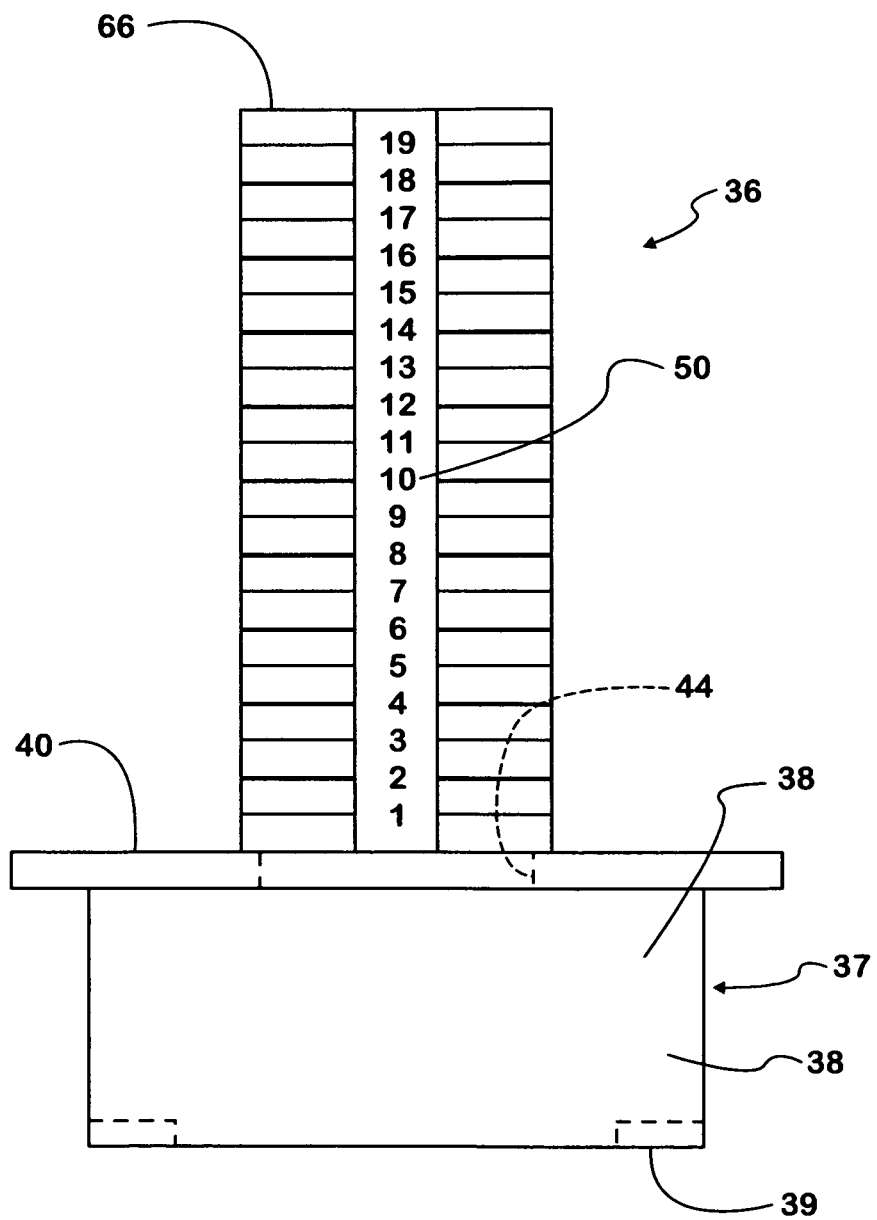
FIG. 2 shows the first embodiment penetrator holder or launch tube with a spacer cylindrical base for mounting the penetrator of FIG. 1 a fixed distance above and onto a standard cup.

FIG. 2 shows the launch tube or penetrator holder 36 for mounting the drop weight penetrator into a sample container.

Figure 3:
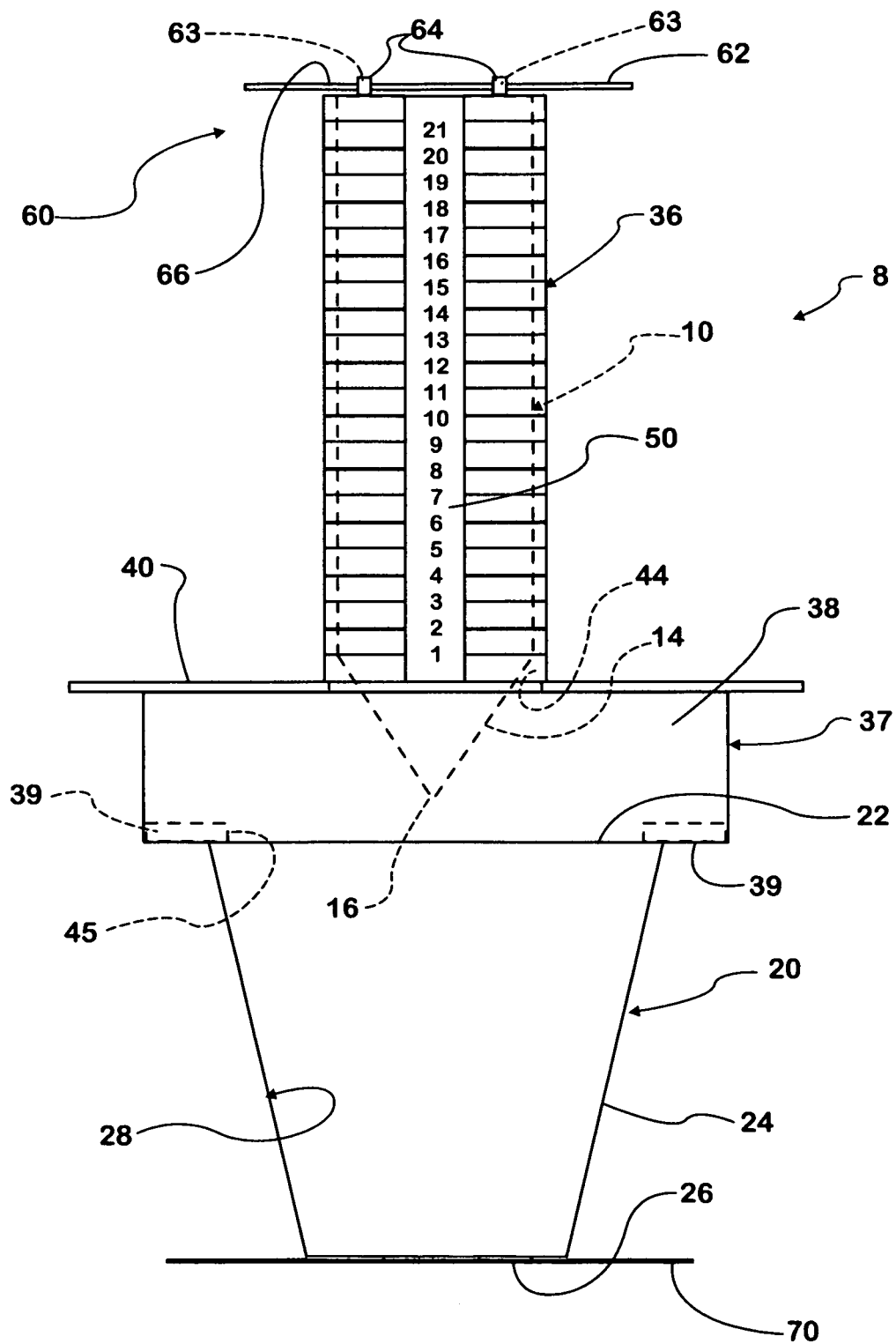
FIG. 3 shows the sample container (in this instance a standard disposable and transparent 10 oz. cup), the penetrator holder mounted on the standard cup, and the penetrator shown therein in dashed lines.

Referring to FIG. 3, the standard sample container is, in this instance, a standard 10 oz. disposable and transparent cup 20, having a top rim 22, a tapered sidewall 24 and a bottom 26, with a fix, known interior volume 28. The test apparatus and method of the present invention is not restricted to a special type/size of cup as long as the cup used is deep enough to keep the penetrator device from hitting the bottom. As for the cup size, one can use a 10-20 ounce size cup or preferably the same size cup the operator or customer uses in making an FCB or non FCB.

The penetrator holder 36 is mounted upon the top or rim 22 of a spacer portion 37. For this purpose the holder 36 has a lower, in this instance, flat wall 40 for joining to and locating the holder 36 on the top of the integral cylindrical base or spacer 37. The annular bottom wall 39 joined to the spacer's 37 cylindrical wall 38 engages the rim 22 of the cup 20 and is open to at 45 to permit the penetrator to pass and also permit overflow of beverage as the penetrator enters a beverage full (struck level) cup. Likewise, the bottom wall 38 has a center opening 44 (shown in dotted lines) through which the penetrator 10, when dropped, can free fall or pass. The holder 36 is of a fixed known height (say from about 6 inches to about 8 inches, plus or minus one inch or preferably about 6⅝ inches plus or minus ¼ inch and sized to hold the penetrator from to 2 to ⅝ inch, and the particular distance is determined by the product type above the beverage top surface in its sample cup so the energy of the penetration is also fixed when dropped from this height. For example, it could have a height of 1.4 inches above the sample surface (top of the sample container). The holder 36 can have a penetration indicia or scale 50, say in inches or fractions thereof or in centimeters or fractions thereof, or any other arbitrary scale or manner. Alternatively, the scale could be on the penetrator, itself, or even on the sample cup.

Figure 4:
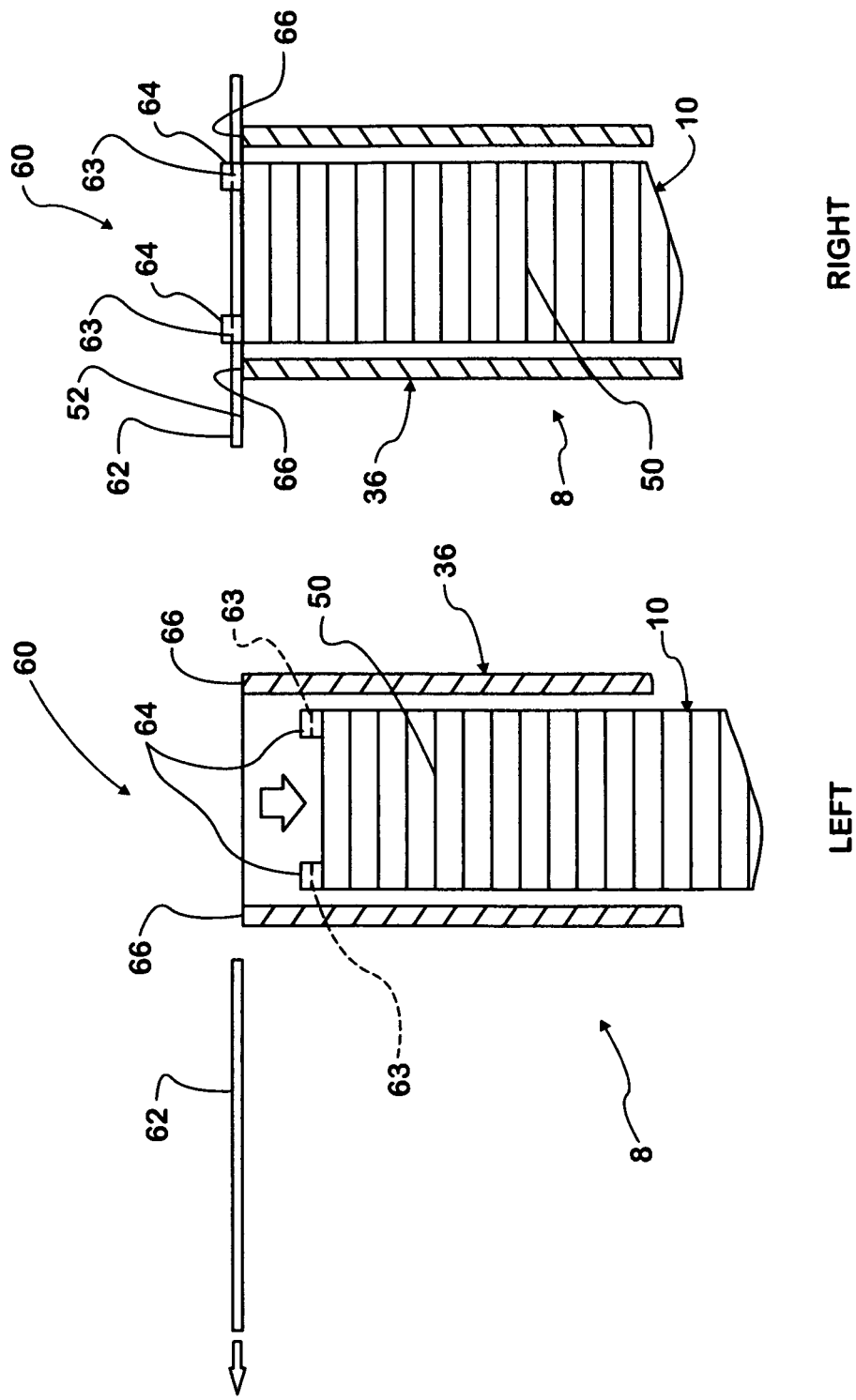
FIG. 4 (right unreleased-left released) shows one form of trigger or release means for the penetrator (partially shown).

Referring to FIGS. 3 and 4, a first type release or trigger means 60 is shown. The penetrator 10 is released from the holder 36 by the trigger means 60. The trigger means 60 could be in the form a rod or wire 62 that engages the penetrator at pin carriers 64 and the holder 36 at its top rim 66. The pin 62 fits in openings 63 in pin carrier portions 64 on the penetrator 10 (as shown on the right side of FIG. 4). The release pin 62 can be supported by the upper rim 66 of the launch tube or holder 36. When the pin 62 is pulled out of the pin carrier portions 64, the (left side of FIG. 4), the penetrator 10 will drop into the beverage (see FIG. 5).

Figure 5:
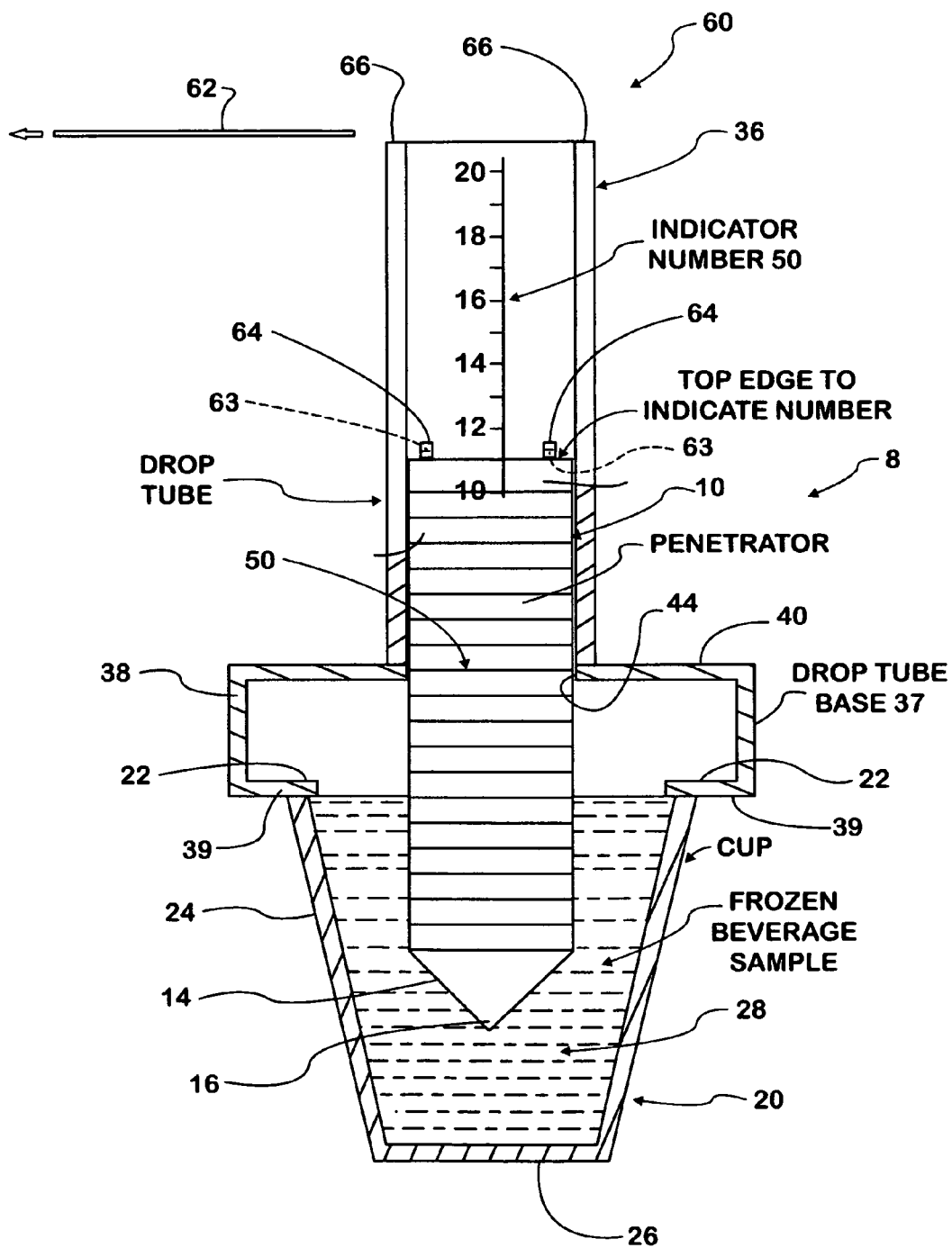
FIG. 5 shows the dropped penetrator (similar to that of FIG. 4) embedded into the beverage sample.

Referring to FIG. 5, with the pin 62 pulled out the penetrator drops into the beverage in the cup at the bottom of the launch tube and the excess forced out by the penetrator flows out of the cup. The penetrator holder 36, in this instance, carries the indicia 50, but they could have alternatively appeared on the penetrator. The depth of penetration indicates the stiffness of the beverage. A greater depth of penetration indicates a less "stiff" beverage. Conversely a smaller depth of penetration indicates a stiffer beverage. In FIG. 5 the indicia 50 on the holder has higher numbers at the top (here 20) and lower at the bottom (here 10) so that, in this instance, a "20" reading would indicate a beverage stiffer than a "10", and a "10" would indicate a greater drop than a "20". The scale is arbitrary, and any could be utilized. For example, another indicator scale is shown in FIG. 6, being from "15" plus to zero "0".

Figure 6:
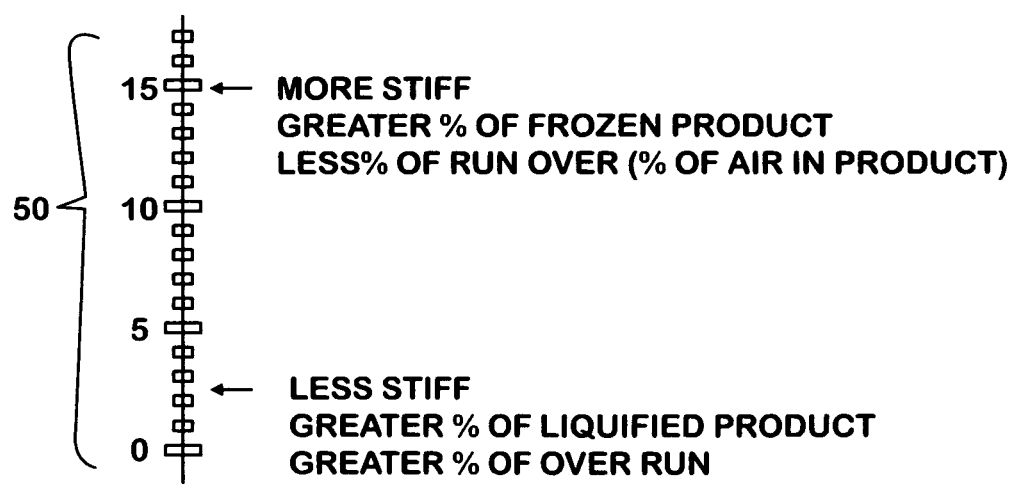
FIG. 6 shows one form of the "guidance table" for relating test data to FCB characteristics for FCB machine adjustment.
Figure 10:
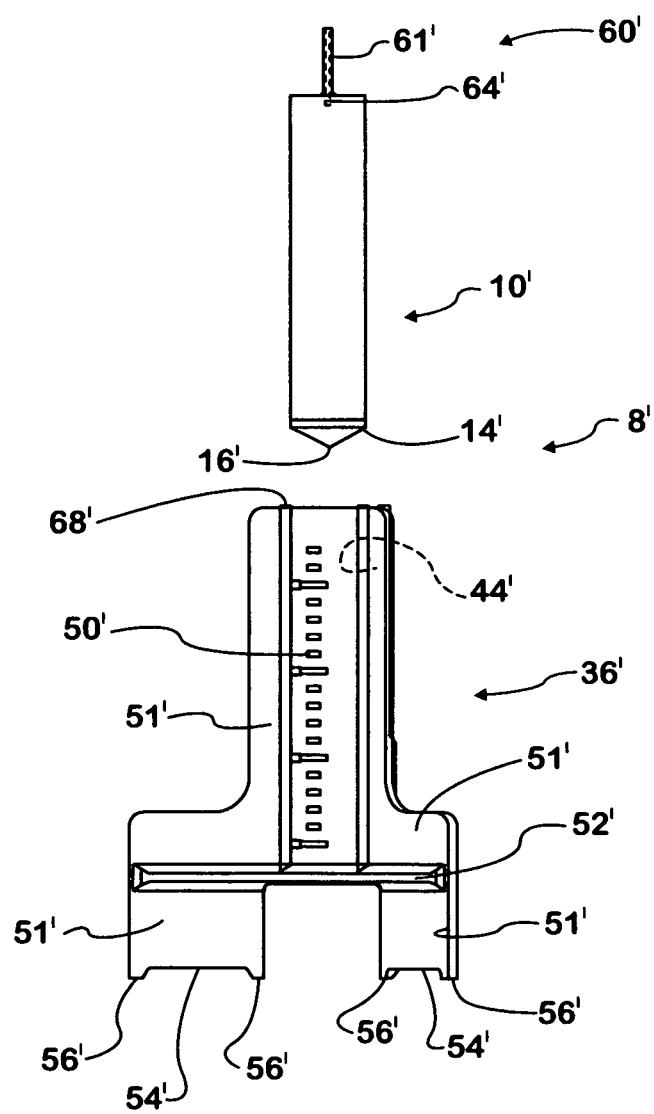
FIG. 10 is an exploded elevational view of the penetrator prior to loading into the launch tube of the second embodiment.

As shown in FIG. 6, the less the penetration or drop of the penetrator into the beverage indicates a more stiff beverage, with a greater percentage of frozen product therein or less percentage of overrun (percent of gas or air in the product). The greater the penetration or drop, the less stiff the product is, the greater percent of liquefied product therein or greater percentage of overrun. The penetrator test is used to test the product and to keep it and the penetration consistent and to help make corrections in the above percentages via refrigeration and/or gas or air inclusion.

The method of using the apparatus to perform the stiffness test is as follows:

drawing off a sample frozen beverage in the sample container 20.
striking off the sample at the rim or top level of the sample container 20.
taking the temperature of the sample (testing should be done at a consistent chosen temperature to limit this variable).
placing the holder 36 on the cup 20.
placing a clean penetrator 10 in the holder 36.
setting up the trigger or release 60 (pin 62 in openings 63) to hold the penetrator 10 in place on the holder 36.
setting off the release 60 (pull out the pin 62)
dropping the penetrator 10 onto the sample by gravity.
noting or measuring the depth of penetration of the penetrator 10 into the sample using, preferably the scale 50.
if need be, adjusting the frozen beverage and/or the machine producing it using the information provided by the penetrator depth and guidance table (FIG. 6) by adjusting refrigeration and/or gas or air inclusion or other factors to provide a consistent stiffness to the frozen beverage be it carbonated or noncarbonated.
then cleaning the equipment (for reuse).

Referring to FIGS. 7 to 14 a second preferred embodiment 8' for carrying out the method and apparatus of the present invention is illustrated. To the extent the embodiment shown in FIGS. 7 to 14 are similar to the embodiment shown in FIGS. 1 to 6, the same reference numerals but primed are used in the drawings. To the extent there are differences, different primed reference numerals are used.

Referring to FIGS. 7-14, a second preferred embodiment 8' apparatus of the present invention includes a penetrator 10', which is of a fixed cross-section, such as round or square) of a fixed length, the length is determined by the product type 6⅛ inches plus or minus ¼ inch for milk products, 6 inches plus or minus ¼ for yogurt products and 4¾ inches plus or minus ¼ inch for fruit slush so as to give a desired drop of the penetrator point down into the sample surface, a fixed known weight (say 70 or 100 grams), and a fixed standardized penetrator end 14', having a downward pointed end 16' having a downward pointed end 16' as discussed above dependent on beverage type.

Figure 11:
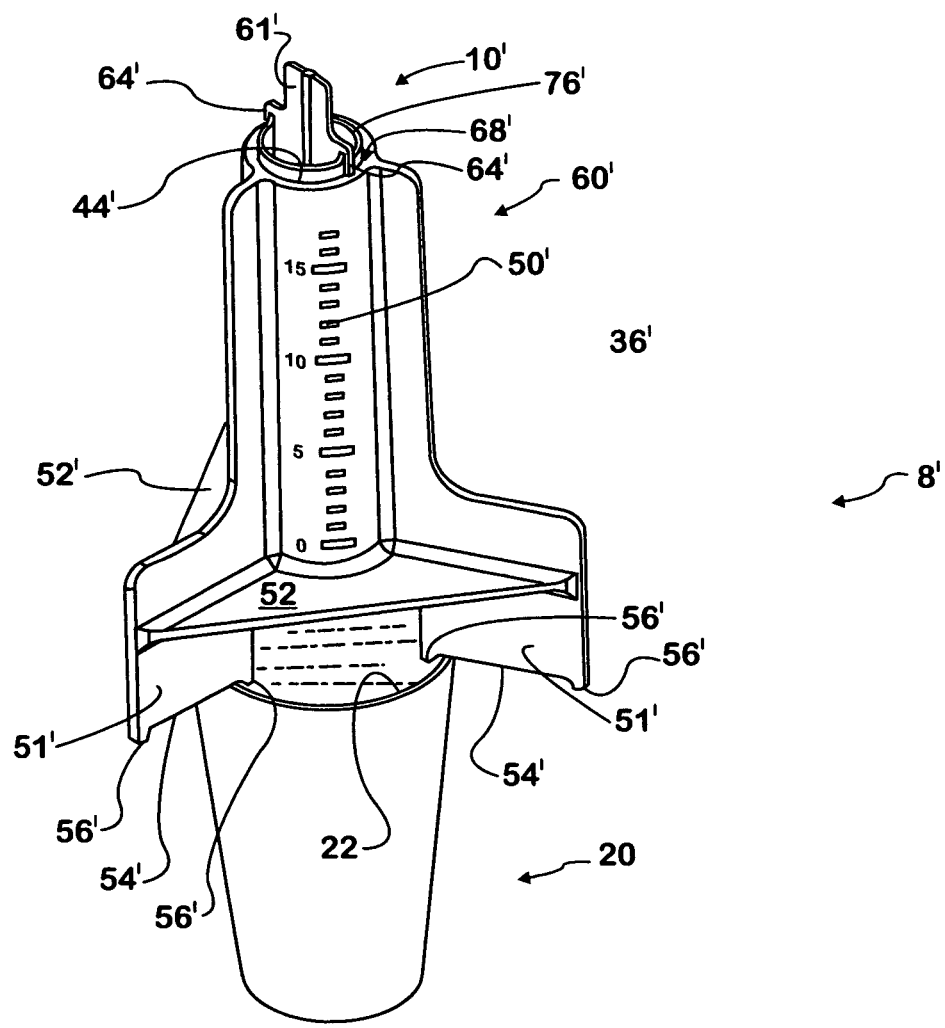
FIG. 11 is a perspective view of the penetrator loaded in the launch tube of the second embodiment, now all mounted on the beverage filled cup.
Figure 14:
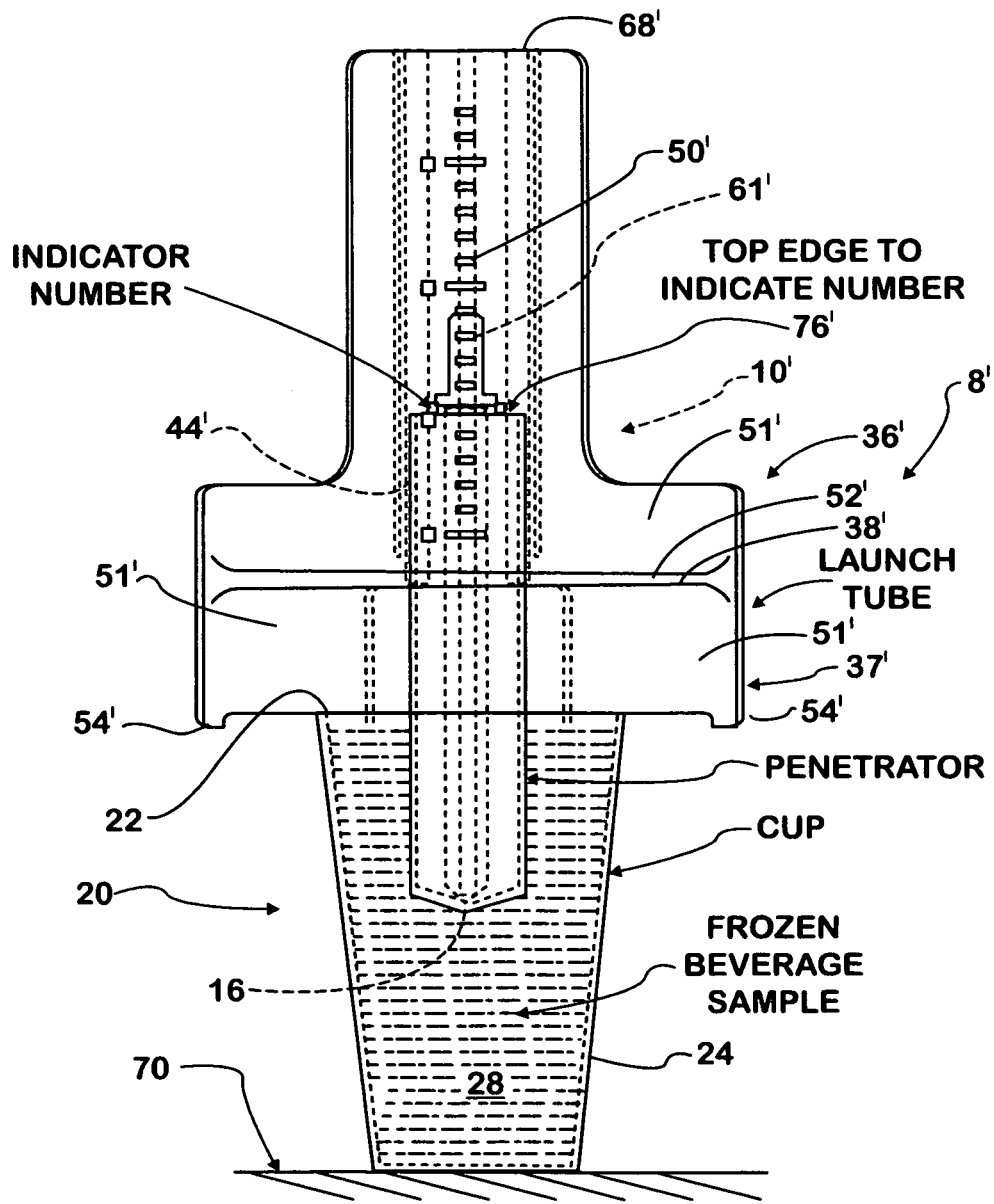
FIG. 14 is a cross sectional view of the second embodiment showing how the launched penetrator penetrates the contents in the disposable cup giving a reading on the indicia and top edge of the penetrator of the consistency of the beverages.
Figure 25A:
FIG. 25A is an alternative wording for the indicia like that shown in FIG. 25.
Figure 25:
FIG. 25 is a top view of the embodiment shown in FIG. 24.

FIGS. 7, 8, and 11 to 14 show the launch tube or penetrator holder 36' for mounting the penetrator 10' on a sample container 20. The test container can be the same type as for first embodiment 8. Referring to FIGS. 7, 11 and 14, the standard sample container is, in this instance, again a standard 10 oz. cup 20, having a top rim 22, a tapered sidewall 24 and a bottom 26, with a fix, known interior volume 28. The test apparatus and method of the present invention is not restricted to a particular or special type/size of cup as long as the cup size is not changed between tests and the cup used is deep enough to keep the penetrator device from hitting (say at least one half inch off) the bottom. As for the cup size, one can use a 10-20 ounce size cup, or preferably the same size cup the operator or customer uses to draw an FCB or non FCB beverage.

In the preferred second embodiment 8', the penetrator holder 36' is mounted upon the top or rim 22 of the cup 20. For this purpose the holder 36' has three legs 51' for locating the holder 36' on the top or rim 22 of the cup 20. The legs 51' are joined to a horizontal web member 52' for added support for the legs. The lower edge 54' of each leg has two downward prongs 56' to locate and help center a cup and keep the holder from slipping off the cup. The launch tube has center opening 44' (shown in dotted lines) through which the penetrator 10', when dropped, can fall or pass.

The trigger or release means 60' is shown in FIG. 8 in enlarged form and includes one or more finger tabs 61' on the penetrator 10' to help rotate the penetrator 10' (from a stable to released position). The penetrator 10' also has side tabs or ears 64' extending upward to hold the penetrator 10' on the top of the rim 68' (see FIGS. 11 and 13) of the launch tube until triggered or released.

Referring to FIG. 9, to cooperate with the tabs or ears 64, at least one, and in this instance, a pair of slots 72' (these would normally be a slot for each ear) are formed in the interior side wall of the launch tube. These slots 72' and ears 64' are sized to permit the penetrator to freely and easily fall down once the penetrator 10' is rotated by finger pressure turning the tab 61' so that the ears 64' align with and fall into the vertical slots 72'. Of course the tabs and slots could be reversed with the slots formed in the penetrator and the tabs or ears formed on the launch tube. Other suitable trigger means could be provided as long as it consistently launch the penetrator from its holder into the sample.

As noted the penetrator holder 36' is provided with three legs 51', which at the bottom contact at 54' the rim 22 of the disposable cup 20. To ensure consistency, the cup 20 with the launch tube 36' thereon should be placed on a horizontal level surface 70' (FIG. 14) or at least one close to level. The penetrator 10' is then placed in the launch tube 36' with the ears 64' and slots 72' misaligned to hold the penetrator on the launch tube. Then the finger tab 61' is turned between a finger and thumb (without gripping) so the ears 64' and slots 72' align, and the penetrator 10' drops into the sample in the cup 20 causing some of the beverage to overflow the rim of the cup 20.

Similarly, as for the first embodiment 8, the second embodiment 8', the holder 36' is of a fixed known height so the energy of the penetration is also fixed when dropped from this height. For example, it could have a height of 6⅝ inches plus or minus ¼ inch above the sample surface (top of the sample container). The holder 36' can have a penetration scale 50', say in inches or fractions thereof or in centimeters or fractions thereof, or any other arbitrary fixed manner. Alternatively, the scale could be on the penetrator, itself.

The method for carrying out the present invention using the second embodiment 8', is similar to that for the first embodiment.

The method of using the apparatus to perform the stiffness test is as follows:

drawing off a sample frozen beverage in the sample container 20.
striking off the sample at the rim or top level of the sample container 20.

taking the temperature of the sample.

placing the holder 36' on the cup 20.

placing a clean penetrator 10' in the holder 36'.

setting up the trigger or release means 60' which could be in the form of finger tab 61', ears 64' and slots 72' (misaligned) to hold the penetrator 10' in place on the holder 36'.

setting off the trigger or release means 60' (by turning tab 61' to cause the ears 64' and slots 72' to align) to drop the penetrator 10' onto the sample by gravity.

noting or measure the depth of penetration of the penetrator 10 onto the sample using, preferably the scale 50' on the holder 36'. The top edge 76 of the penetrator 10' could be the movable indicia read against the scale 50'.

if need be, adjusting the frozen beverage or the machine making the same by using the information provided by the penetrator depth and guidance table (see FIG. 6) to provide a consistent stiffness to the frozen beverage.

then cleaning the equipment (for reuse).

Figure 15:
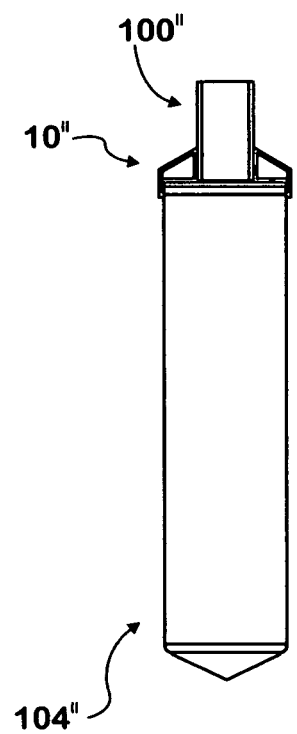
FIG. 15 is an elevational view of a third embodiment penetrator assembled from two pieces, top and bottom, for use with "dairy" type beverages.

Referring to FIG. 15 an assembled penetrator 10" for use with dairy type beverages is shown and compresses a top piece 100" shown in FIGS. 16 to FIGS. 19 which is used with and assembled onto a bottom piece 104" shown in FIG. 15, and FIG. 20 to FIG. 23. The top piece 100" can carry beverage type indicia 106", in this instance, for dairy slushies (see FIG. 19). To prevent mix-up the set bottom of the top piece 100" and the top of the bottom piece 104" are sized or dimensioned to fit only with one another, and not to the below described components for the fruit type slushies shown in FIGS. 24-30. To assist operators, the two top pieces, bottom pieces, or both of penetrators dairy and non-dairy can also be of different colors.

Figure 24:
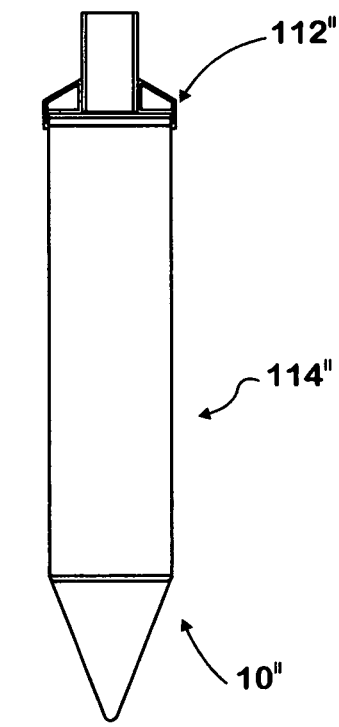
FIG. 24 is an elevational view of another embodiment of penetrator assembled from two pieces, a top and bottom, for use with non-dairy, fruit type slush beverages.
Figure 20:
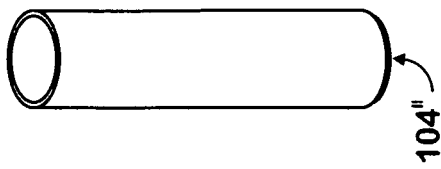
FIG. 20 is a perspective view of the bottom piece of the penetrator shown in FIG. 15.
Figure 22:
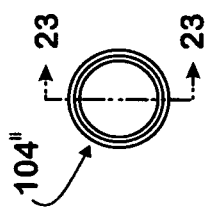
FIG. 22 is a top view of the piece shown in FIG. 20.
Figure 21:
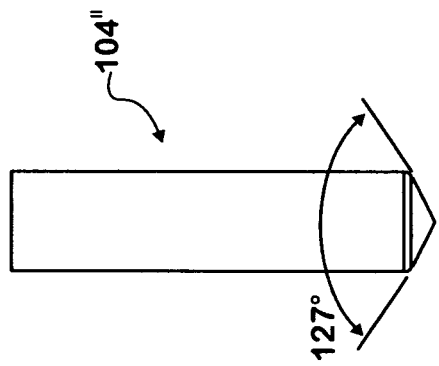
FIG. 21 is a front elevational view of the piece shown in FIG. 20.
Figure 23:
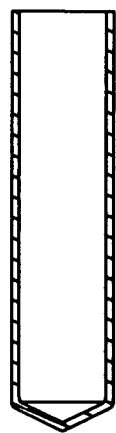
FIG. 23 is a cross-sectional view taken along the line 23-23 of FIG. 22.
Figure 26:
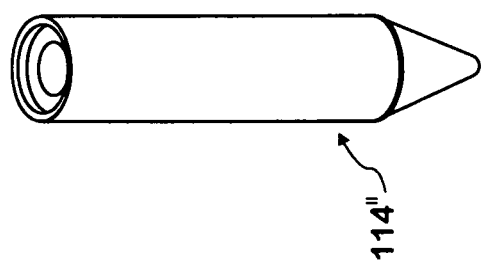
FIG. 26 is a perspective view of the bottom piece shown in FIG. 24.
Figure 29:
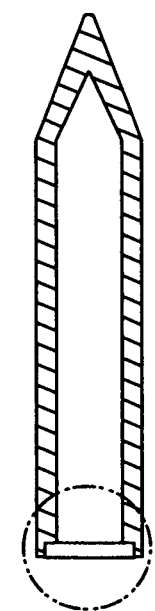
FIG. 29 is a cross-sectional view of the piece shown in FIG. 26 taken on the line 29-29 of FIG. 28.
Figure 27:
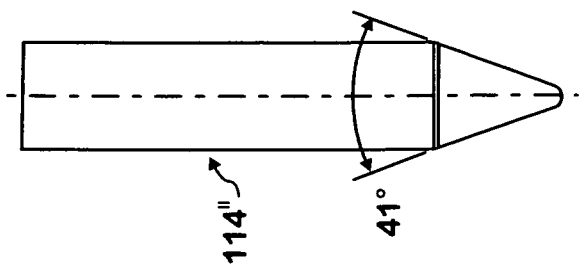
FIG. 27 is an elevational view of the bottom piece shown in FIGS. 24 and 26.
Figure 28:
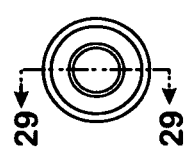
FIG. 28 is a top view of the piece shown in FIG. 27.
Figure 30:
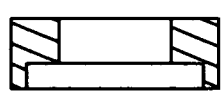
FIG. 30 is an enlarged, cross-sectional view of the upper portion detail of the bottom piece circled in FIG. 29.

Referring to FIG. 24, a penetrator 10" is shown for use with fruit type slushies, and so assembled and made from a top piece 112" similar to that shown in FIGS. 16 to 19, but different in that it carries a fruit type "non-dairy" indicia, maybe of a different color, and has size and dimensions that permit to be assembled only to its bottom piece 114" shown in FIG. 26 to FIG. 30, and not that shown in FIG. 20 to FIG. 30.

The top 100" or 112" and bottom 104" or 114", respectively pieces can be held together by various means such as adhesives and/or epoxy. As the beverage samples are just for test purposes and are disposed of, the adhesive or epoxy means need not be safe for human consumption, although such feature could be easily provided should it be so desired.

With respect to the point of the angle of 40 plus or minus 10 degrees to 140 plus or minus 10 degrees such could be provided on any penetrator of the present Invention. As to the lengths of the penetrator and the various drop heights of the penetrator into the sample such could be provided for any of the penetrators of the present invention.

The method of use of the penetrations 10' or 10" in FIGS. 15-23 or FIGS. 24-30 is similar to that for the earlier described embodiments and would be used with a launch tube or holder similar to those earlier described.

While the preferred embodiments and elements of the apparatus and steps of the method of the present invention have been disclosed and described, equivalent elements and/or equivalent steps would also fall within the scope of the following, or in the future to be appended, claims.

What we claim is:

1. An apparatus for determining the stiffness of a frozen (semi-frozen) beverage, comprising a standard sample test container, a penetrator for penetrating the beverage, a penetrator holder for holding the penetrator a fixed height above the sample test container, wherein said penetrator holder is capable of standing vertically on said standard sample test container, and a release means for releasing and dropping the penetrator into the standard sample test container, whereby the stiffness of a sample of the frozen beverage in said standard sample test container may be determined.

2. An apparatus as in claim 1, wherein said penetrator has a mass of 70 to 100 grams.

3. An apparatus as in claim 2, wherein said penetrator has an angle of 40 to 140 degrees, said release means being a mechanical means for releasing the penetrator to fall, said penetrator holder being tubular and said penetrator being tubular and fitting inside of said penetrator holder, one of said penetrator and penetrator holder having graduations to assist in determining the position the penetrator sinks into the sample, said standard sample test container being of 10 to 20 ounce size, said penetrator holder being capable of standing vertically above said standard sample test container, and said graduations on one of said penetrator and penetrator holder relates to information on how to adjust the frozen beverage to achieve a desired stiffness.

4. An apparatus as in claim 3, wherein said release means includes a pin engaging said penetrator and penetrator holder, and movement of said pin out of said penetrator holder drops said penetrator from said penetrator holder into a sample.

5. An apparatus as in claim 3, wherein release means comprises at least one slot in one of the penetrator and penetrator holder and at least one rib on the other of said penetrator and penetrator holder, said penetrator falling when said rib is aligned to pass through said slot.

6. An apparatus as in claim 5, wherein said penetrator has an extended top tab for rotating the penetrator in the penetrator holder to align said rib and slot.

7. An apparatus as in claim 1, wherein said penetrator has a penetrating lower end of an angle of 40 to 140 degrees.

8. An apparatus as in claim 1, wherein said release means is a mechanical means for releasing the penetrator to fall downward.

9. An apparatus as in claim 8, wherein said release means includes a pin engaging said penetrator and penetrator holder, and movement of said pin drops said penetrator from said penetrator holder into a sample.

10. An apparatus as in claim 8, release means comprises at least one slot in one of the penetrator and penetrator holder and at least one rib on the other of said penetrator and penetrator holder, said penetrator falling when said rib is aligned to pass through said slot.

11. An apparatus as in claim 10, wherein said penetrator has an extended top tab for rotating the penetrator in the penetrator holder to align said rib and slot.

12. An apparatus as in claim 1, wherein said penetrator holder is tubular and said penetrator is tubular and fits inside of said penetrator holder.

13. An apparatus as in claim 12, wherein one of said penetrator and penetrator holder is graduated to assist in determining the position the penetrator sinks into the sample.

14. An apparatus as in claim 1, wherein said standard sample test container is of 10 to 20 ounce size.

15. An apparatus as in claim 1, comprising graduations on one of said penetrator and penetrator holder said graduations relating to information on how to adjust the frozen beverage to achieve a desired stiffness.

16. Apparatus as in claim 1, wherein one of said penetrator and penetrator holder has indicia indicating on what beverage they are to be used.

17. An apparatus for determining the stiffness of a frozen (semi-frozen) beverage, comprising a standard sample test container, a penetrator for penetrating the beverage, a penetrator holder for holding the penetrator a fixed height above the sample test container, and a release means for releasing and dropping the penetrator into the standard sample test container, whereby the stiffness of a sample of the frozen beverage in said standard sample test container may be determined, wherein said penetrator holder has at least three lower legs for holding said holder above the standard sample test container.

18. Apparatus as in claim 17, wherein said legs are approximately 120 degrees apart and engage a top of the standard sample test container.

* * * * *